(12) United States Patent
Burkett et al.

(10) Patent No.: US 12,220,259 B2
(45) Date of Patent: Feb. 11, 2025

(54) INTRAVASCULAR DEVICES SYSTEMS AND METHODS WITH AN ADHESIVELY ATTACHED SHAPING RIBBON

(71) Applicant: KONINKLIJKE PHILIPS N.V., Eindhoven (NL)

(72) Inventors: David Holt Burkett, Panama City Beach, FL (US); Samuel Ritter, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 713 days.

(21) Appl. No.: 15/745,534

(22) PCT Filed: Jul. 1, 2016

(86) PCT No.: PCT/IB2016/053957
§ 371 (c)(1),
(2) Date: Jan. 17, 2018

(87) PCT Pub. No.: WO2017/013512
PCT Pub. Date: Jan. 26, 2017

(65) Prior Publication Data
US 2018/0214082 A1    Aug. 2, 2018

Related U.S. Application Data

(60) Provisional application No. 62/193,988, filed on Jul. 17, 2015.

(51) Int. Cl.
*A61B 5/00* (2006.01)
*A61B 5/0215* (2006.01)
(Continued)

(52) U.S. Cl.
CPC .......... *A61B 5/6851* (2013.01); *A61B 5/0215* (2013.01); *A61B 5/026* (2013.01);
(Continued)

(58) Field of Classification Search
CPC ..... A61B 5/6851; A61B 5/0215; A61M 25/09
See application file for complete search history.

(56) References Cited

U.S. PATENT DOCUMENTS 4,953,553 A * 9/1990 Tremulis ............... A61B 5/0215
600/434
5,125,137 A 6/1992 Corl
(Continued)

FOREIGN PATENT DOCUMENTS

| JP | 2010259624 A | 11/2010 |
|---|---|---|
| WO | 2015059578 A2 | 4/2015 |
| WO | 2016165943 A1 | 10/2016 |

*Primary Examiner* — Alex M Valvis
*Assistant Examiner* — Karen E Toth (57) ABSTRACT

The present disclosure is directed to intravascular devices, systems, and methods having a core member coupled to a shaping ribbon with an adhesive. In some aspects, a sensing guide wire is provided. The sensing guide wire can include a flexible elongate member; and a sensing element coupled to a distal portion of the flexible elongate member, wherein the distal portion of the flexible elongate member includes: a core member; and a shaping ribbon fixedly secured to the core member by an adhesive and at least one connecting sleeve. In other aspects, methods of forming a sensing guide wire are provided.

20 Claims, 8 Drawing Sheets

(51) Int. Cl.
 *A61B 5/026* (2006.01)
 *A61M 25/09* (2006.01)
 *B29C 65/00* (2006.01)
 *B29C 65/72* (2006.01)

(52) U.S. Cl.
 CPC ......... *A61B 5/6852* (2013.01); *A61B 2562/12* (2013.01); *A61M 25/09* (2013.01); *A61M 2025/09075* (2013.01); *A61M 2025/09108* (2013.01); *B29C 65/72* (2013.01); *B29C 66/7428* (2013.01)

(56) References Cited

U.S. PATENT DOCUMENTS

| | | | |
|---|---|---|---|
| 5,873,835 A | 2/1999 | Hastings | |
| 6,106,476 A | 8/2000 | Corl | |
| 6,551,250 B2 | 4/2003 | Khalil | |
| 6,645,159 B1* | 11/2003 | Burkett | A61M 25/09 600/585 |
| 2001/0039412 A1* | 11/2001 | Fariabi | A61M 25/09 604/170.03 |
| 2002/0143360 A1* | 10/2002 | Douk | A61B 17/12172 606/200 |
| 2004/0102720 A1 | 5/2004 | Kellerman | |
| 2004/0167443 A1* | 8/2004 | Shireman | A61M 25/09 600/585 |
| 2005/0124917 A1* | 6/2005 | Skujins | A61M 25/09 600/585 |
| 2006/0122537 A1* | 6/2006 | Reynolds | A61L 31/022 600/585 |
| 2006/0129041 A1 | 6/2006 | Ellis | |
| 2006/0144408 A1* | 7/2006 | Ferry | A61M 25/0054 128/899 |
| 2008/0045908 A1* | 2/2008 | Gould | A61M 25/09 604/272 |
| 2009/0043228 A1* | 2/2009 | Northrop | C21D 7/06 600/585 |
| 2009/0292225 A1* | 11/2009 | Chen | A61M 25/09033 600/585 |
| 2011/0015618 A1 | 1/2011 | Satou | |
| 2011/0054351 A1* | 3/2011 | Fox | A61L 27/06 600/585 |
| 2011/0245808 A1* | 10/2011 | Voeller | A61M 25/0054 604/528 |
| 2012/0289938 A1* | 11/2012 | Northrop | A61M 25/09 604/528 |
| 2014/0005543 A1 | 1/2014 | Burkett | |
| 2014/0005558 A1* | 1/2014 | Gregorich | A61B 5/02154 600/480 |
| 2014/0180141 A1 | 6/2014 | Millett | |
| 2014/0187874 A1 | 7/2014 | Millett | |
| 2014/0187980 A1 | 7/2014 | Burkett | |
| 2014/0187981 A1 | 7/2014 | Millett | |
| 2014/0187984 A1 | 7/2014 | Burkett | |
| 2015/0045695 A1* | 2/2015 | Simpson | B23K 20/002 228/101 |
| 2015/0057532 A1* | 2/2015 | Belleville | A61M 25/09 600/424 |
| 2015/0217090 A1 | 8/2015 | Burkett | |
| 2015/0314109 A1* | 11/2015 | Minar | A61B 1/01 604/528 |
| 2016/0022215 A1 | 1/2016 | Henderson | |

\* cited by examiner

INTRAVASCULAR DEVICES SYSTEMS AND METHODS WITH AN ADHESIVELY ATTACHED SHAPING RIBBON

CROSS-REFERENCE TO PRIOR APPLICATIONS

This application is the U.S. National Phase application under 35 U.S.C. § 371 of International Application No. PCT/IB2016/053957, filed on Jul. 1, 2016, which claims the benefit of U.S. Provisional Patent Application No. 62/193,988, filed on Jul. 17, 2015. These applications are hereby incorporated by reference herein.

TECHNICAL FIELD

The present disclosure relates to intravascular devices, systems, and methods. In some embodiments, the intravascular devices are guide wires that include a core member coupled to a shaping ribbon with an adhesive. In some instances, the adhesive is introduced within one or more connecting sleeves positioned around the core member and the shaping ribbon.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is Fractional Flow Reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guide wires are utilized to measure the pressure within the blood vessel, visualize the inner lumen of the blood vessel, and/or otherwise obtain data related to the blood vessel. Guide wires can include pressure sensors, imaging elements, and/or other electronic, optical, or electro-optical components to obtain such data. A core member generally extends along the length of the guide wire. The one or more components are disposed near the distal portion of the core member. The core member is generally formed of elastic and durable material, which allows the guide wire to traverse the tortuous anatomy, such as a patient's blood vessels. However, the elastic and durable characteristics of the core member also make it difficult for a user to shape the distal tip of the guide wire. It can be important for the distal tip of the guide wire to be shapeable so that the guide wire can be steered through tortuous anatomy.

In some instances, the distal tip of the guide wire has been formed by attaching a shaping ribbon to the distal end of the core member using tack solder. A problem with existing distal tips is that a highly corrosive flux material is used to prepare the core member for the tack soldering process. In addition to complicating the manufacturing process, the corrosive flux must be completely cleaned off after soldering to avoid corrosion of the base materials of the guide wire that could result in device failures, leading to procedure complications and compromising patient safety.

Further, it can be difficult to control the length of a solder joint during the soldering process. The length of the solder joint can impact the smoothness of the transition from the core member to the shaping ribbon. Such unpredictability in the smoothness of the transition can obviate the desired benefits of combining the shaping ribbon with the durable core member.

Accordingly, there remains a need for improved intravascular devices, systems, and methods that include a more reliable and consistent connection between two components at a distal tip.

SUMMARY

The present disclosure is directed to intravascular devices, systems, and methods that include a guide wire having a core member with a shaping ribbon coupled to the core member with an adhesive. In some instances, the adhesive is introduced within one or more connecting sleeves positioned around the core member and the shaping ribbon.

The use of the adhesive to connect the shaping ribbon to the core member eliminates the need to utilize a highly corrosive flux to facilitate soldering and, therefore, eliminates the risks associated with use of the corrosive flux. Removing the need for soldering eliminates a potential failure mode that could occur due to leftover corrosive flux from the soldering process.

Beyond the advantage of eliminating a potential failure mode, there is another benefit to using one or more connecting sleeves and an adhesive to connect the shaping ribbon to the core member. The use of a connecting sleeve allows for a consistent attachment joint length, which facilitates a smooth transition from the core member to the shaping ribbon in a manner that can be repeatedly produced in a predictable manner for consistency from device to device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a flow sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the flexible elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the flexible elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm), approximately 0.018" (0.4572 mm), and approximately 0.035" (0.889 mm). As such, the flexible elongate members incorporating the electronic, optical, and/or electro-optical component(s) of the present application are suitable for use in a wide variety of lumens within a human patient besides those that are part of or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Figure 1:
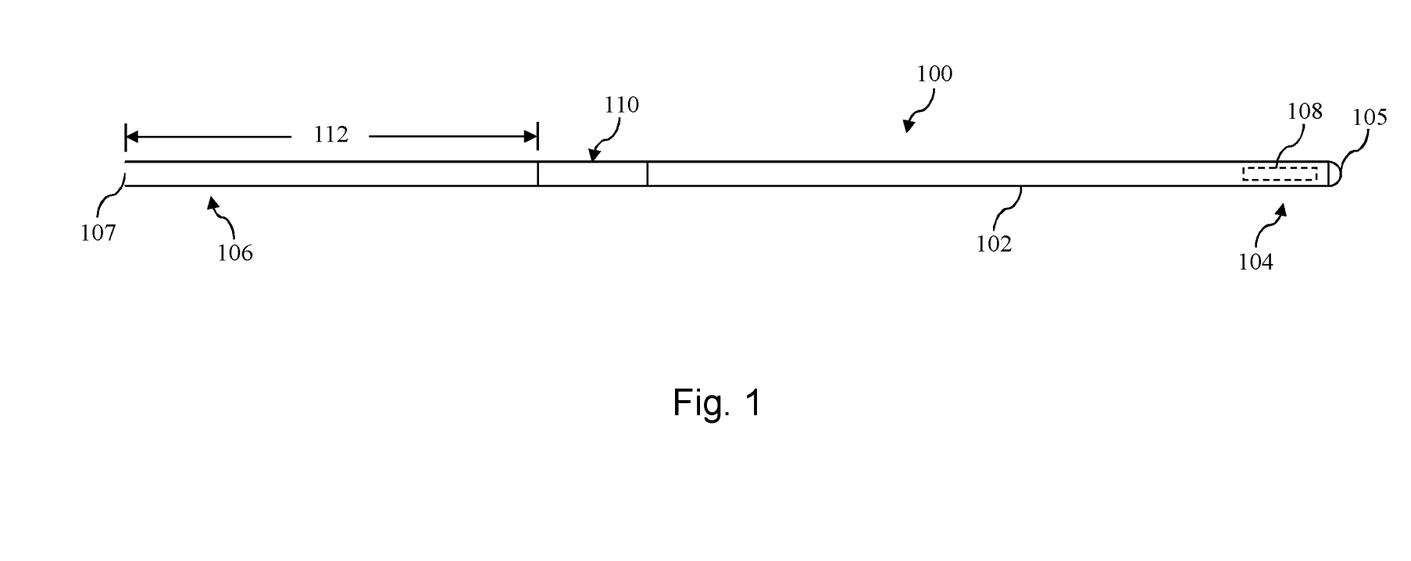
FIG. 1 is a diagrammatic, schematic side view of an intravascular device according to an embodiment of the present disclosure.

Referring now to FIG. 1, shown therein is a diagrammatic, schematic side view of an intravascular device 100 according to an embodiment of the present disclosure. In that regard, the intravascular device 100 includes a flexible elongate member 102 having a distal portion 104 adjacent a distal tip 105 and a proximal portion 106 adjacent a proximal end 107. A component 108 is positioned within the distal portion 104 of the flexible elongate member 102 proximal of the distal tip 105. Generally, the component 108 is representative of one or more electronic, optical, or electro-optical components. In that regard, the component 108 is a pressure sensor, a flow sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 108 is positioned less than 10 cm, less than 5 cm, or less than 3 cm from the distal tip 105. In some instances, the component 108 is positioned within a housing of the flexible elongate member 102. In that regard, the housing is a separate component secured to the flexible elongate member 102 in some instances. In other instances, the housing is integrally formed as a part of the flexible elongate member 102.

The intravascular device 100 also includes a connector 110 adjacent the proximal portion 106 of the device. In that regard, the connector 110 is spaced from the proximal end 107 of the flexible elongate member 102 by a distance 112. Generally, the distance 112 is between 0% and 50% of the total length of the flexible elongate member 102. While the total length of the flexible elongate member 102 can be any length, in some embodiments the total length is between about 1300 mm and about 4000 mm, with some specific embodiments having a length of 1400 mm, 1900 mm, and 3000 mm. Accordingly, in some instances the connector 110 is positioned at the proximal end 107. In other instances, the connector 110 is spaced from the proximal end 107. For example, in some instances the connector 110 is spaced from the proximal end 107 between about 0 mm and about 1400 mm. In some specific embodiments, the connector 110 is spaced from the proximal end by a distance of 0 mm, 300 mm, and 1400 mm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. In some embodiments the electrical conductors are embedded within a core of the flexible elongate member 102. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Similarly, in some embodiments the optical fibers are embedded within a core of the flexible elongate member 102. Further, in some embodiments the connector 110 provides both electrical and optical connections to both electrical conductor(s) and optical communication pathway(s) coupled to the component 108. In that regard, it should be noted that component 108 is comprised of a plurality of elements in some instances. The connector 110 is configured to provide a physical connection to another device, either directly or indirectly. In some instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the flexible elongate member 102 between the connector 110 and the component 108 to facilitate communication between the connector 110 and the component 108. In some instances, at least one of the electrical conductors and/or optical pathways is embedded within the core of the flexible elongate member 102, as described in U.S. Provisional Patent Application No. 61/935,113, filed Feb. 3, 2014, which is hereby incorporated by reference in its entirety. Generally, any number of electrical conductors, optical pathways, and/or combinations thereof can extend along the length of the flexible elongate member 102 between the connector 110 and the component 108, embedded in the core or not. In some instances, between one and ten electrical conductors and/or optical pathways extend along the length of the flexible elongate member 102 between the connector 110 and the component 108. The number of communication pathways and the number of electrical conductors and optical pathways extending along the length of the flexible elongate member 102 is determined by the desired functionality of the component 108 and the corresponding elements that define the component 108 to provide such functionality.

Figure 2:
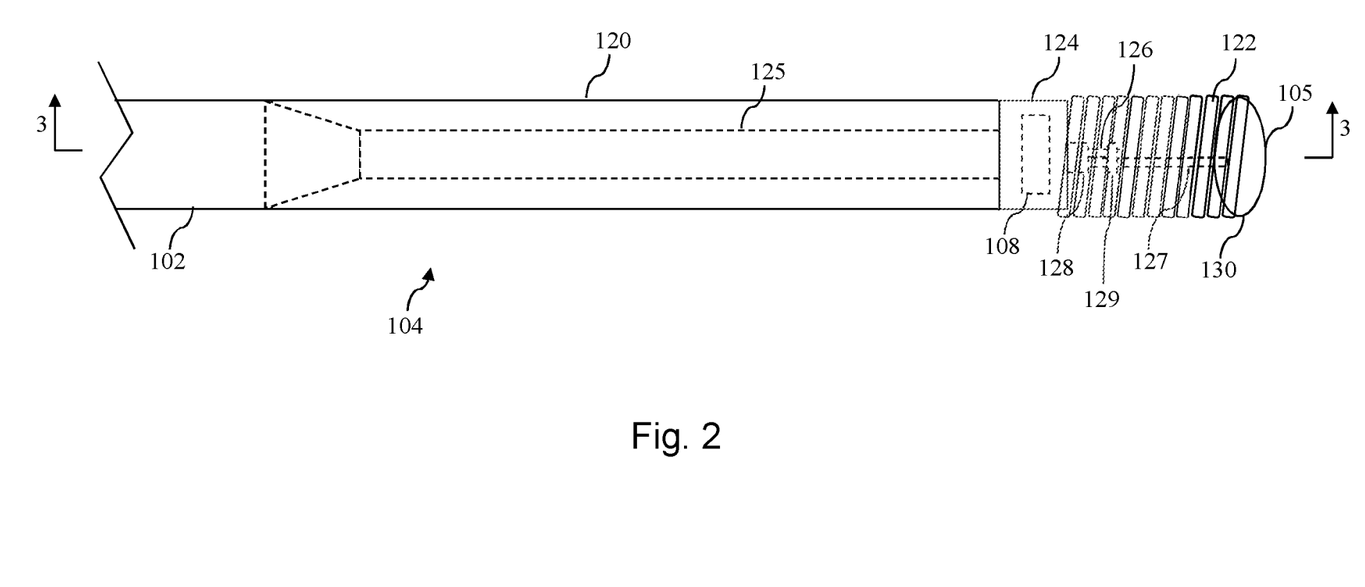
FIG. 2 is a diagrammatic, schematic side view of a distal portion of the intravascular device of FIG. 1 according to an embodiment of the present disclosure.

Referring now to FIG. 2, shown therein is a diagrammatic, schematic side view of the distal portion 104 of the intravascular device 100 according to an embodiment of the present disclosure. As shown, the distal portion 104 includes a proximal flexible element 120 and a distal flexible element 122 on each side of a housing 124 containing component 108. A core member 125 extends through the proximal flexible element 120. Similarly, a core member 126 extends through the distal flexible element 122. In some implementations, the core members 125 and 126 are an integral component (i.e., the core member 125 extends through the housing 124 to define core member 126). In some instances, the core member 126 is coupled to a shaping ribbon 127. As shown, in accordance with the present disclosure, the core member 126 is coupled to the shaping ribbon 127 using adhesive(s) and connecting sleeves 128 and 129. The shaping ribbon 127 can be coupled to various components of the intravascular device 100, including the housing 124 and/or adhesive within and/or surround the housing 124, the core member 126, and/or the distal tip 105 using adhesives, solder, mechanical coupling, and/or combinations thereof. Generally, the core members 125, 126 and the shaping ribbon 127 are sized, shaped, and/or formed out of particular material(s) to create a desired mechanical performance for the distal portion 104 of the intravascular device 100. For example, the core members 125, 126 and the shaping ribbon 127 can be formed from a flexible and/or elastic material, including metals or metal alloys such as nickel titanium or nitinol, nickel titanium cobalt, stainless steel, and/or various stainless steel alloys. In some particular implementations, the core members 125, 126 are formed of nitinol and the shaping ribbon 127 is formed of stainless steel. However, any combination of materials can be used in accordance with the present disclosure. Further, the connecting sleeves 128 and 129 can be formed from any suitable material, including polymers, such as polyimide, pebax, nylon, polyethylene, etc.

The proximal and distal flexible elements 120, 122 can be any suitable flexible element, including polymer tubes, coils, and/or coil-embedded polymer tubes. In the illustrated embodiment the proximal flexible element 120 is a coil-embedded polymer tube and the distal flexible element 122 is a coil. In other embodiments, the proximal flexible element 120 is a polymer tube and the distal flexible element 122 is a coil. In yet other embodiments, other combinations of proximal and distal flexible elements are utilized. As discussed in greater detail below, the proximal and/or distal flexible elements 120, 122 can be at least partially filled with one or more flexible adhesives to improve the mechanical performance and durability of the intravascular device 100. In that regard, in some instances adhesives with varying degrees of durometer are utilized to provide a desired transition in bending stiffness along the length of the intravascular device 100. A solder ball 130 or other suitable element is secured to the distal end of the distal flexible element 122. As shown, the solder ball 130 defines the distal tip 105 of the intravascular device 100 with an atraumatic tip suitable for advancement through patient vessels, such as vasculature. In some embodiments, a flow sensor is positioned at the distal tip 105 instead of the solder ball 130.

The distal portion 104 of the intravascular device 100—as well as the proximal portion 106 and the flexible elongate member 102—may be formed using any suitable approach so long as the distal flexible element 122 contains a shaping ribbon 127 coupled to a core member 126 in accordance with the present disclosure. Accordingly, in some implementations the intravascular device 100 includes features similar to the distal, intermediate, and/or proximal sections described in one or more of U.S. Pat. Nos. 5,125,137, 5,873,835, 6,106,476, 6,551,250, U.S. patent application Ser. No. 13/931,052, filed Jun. 28, 2013, U.S. patent application Ser. No. 14/135,117, filed Dec. 19, 2013, U.S. patent application Ser. No. 14/137,364, filed Dec. 20, 2013, U.S. patent application Ser. No. 14/139,543, filed Dec. 23, 2013, U.S. patent application Ser. No. 14/143,304, filed Dec. 30, 2013, U.S. Provisional Patent Application No. 61/935,113, filed Feb. 3, 2014, U.S. Provisional Patent Application No. 62/027,556, filed Jul. 22, 2014, and U.S. Provisional Patent Application No. 62/147,283, filed Apr. 14, 2015, each of which is hereby incorporated by reference in its entirety.

Figure 3:
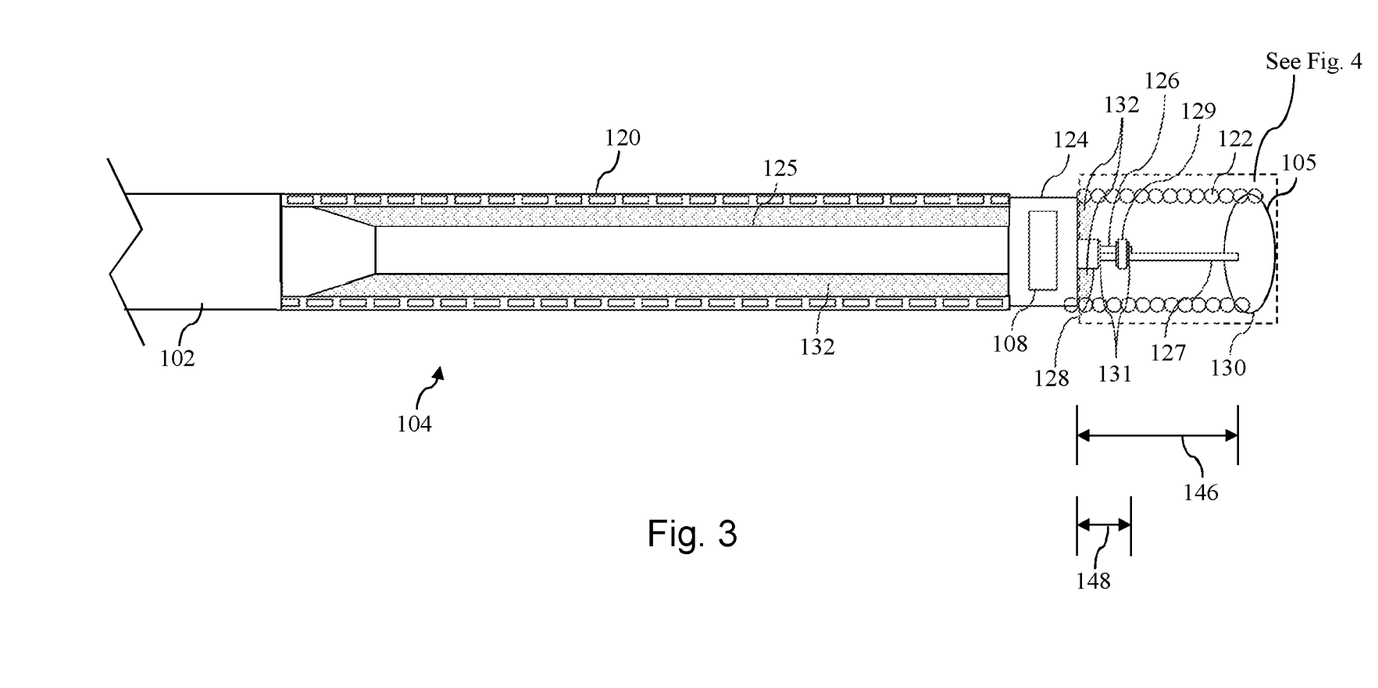
FIG. 3 is a cross-sectional side view of the distal portion of the intravascular device of FIGS. 1 and 2 taken along section line 3-3 of FIG. 2 according to an embodiment of the present disclosure.
Figure 4:
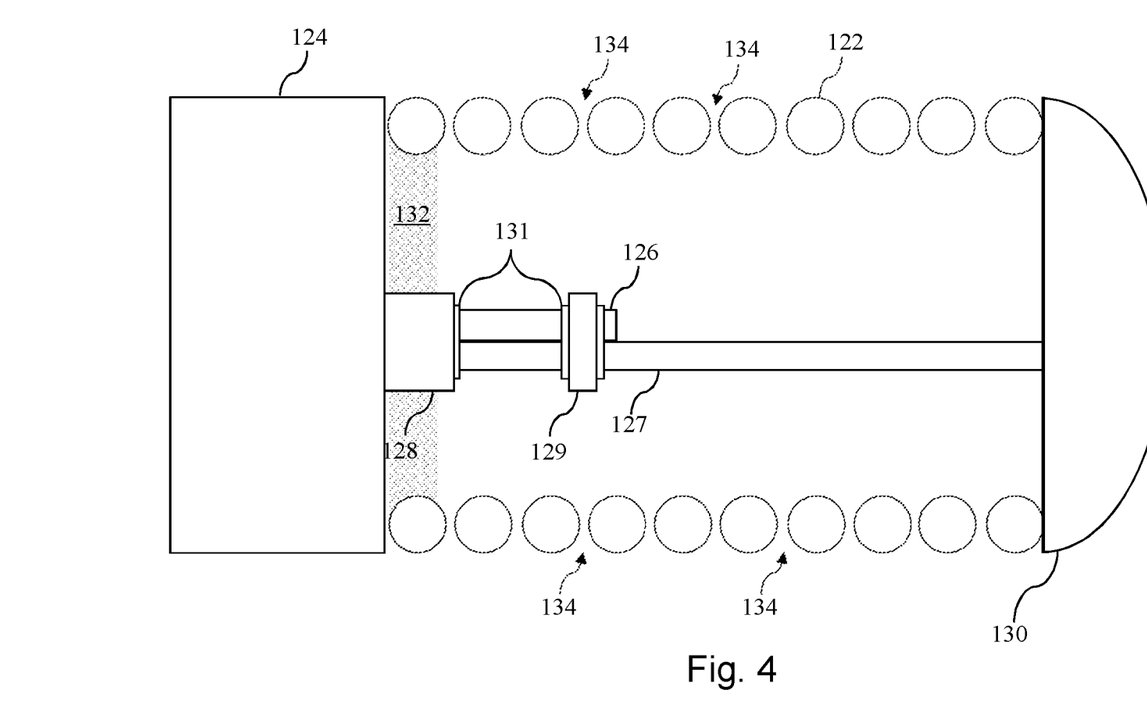
FIG. 4 is a magnified cross-sectional side view of a section of the distal portion of the intravascular device of FIGS. 1-3 according to an embodiment of the present disclosure.

Referring now to FIGS. 3 and 4, shown therein are additional details of the distal portion 104 of the intravascular device 100. In particular, FIG. 3 shows a cross-sectional side view of the distal portion 104 of the intravascular device 100 taken along section line 3-3 of FIG. 2, while FIG. 4 shows a close up cross-sectional side view of a section of the distal portion 104 of the intravascular device 100 according to an embodiment of the present disclosure. As shown, the core member 126 is coupled to the shaping ribbon 127 with the connecting sleeves 128, 129 using an adhesive 131. The adhesive 131 is introduced into the space between the connecting sleeves 128, 129 and the core member 126 and the shaping ribbon 127 and cured to fixedly secure the shaping ribbon 127 to the core member 126. Accordingly, there is no need to couple the core member 126 and the shaping ribbon 127 with tack soldering that requires corrosive flux to be used to prepare the core member 126 for the soldering process. As a result of the use of the connecting sleeves 128, 129 and the adhesive 131, a potential failure mode caused by excess corrosive flux is eliminated.

The connecting sleeves 128, 129 can be sized for consistent connection lengths when coupling the core member 126 and the shaping ribbon 127. In this regard, it can be difficult to create consistent solder joint connection lengths. In contrast, by using connecting sleeves having predetermined lengths, the length of the adhesive connection between the core member 126 and the shaping ribbon 127 can be repeatedly produced with a consistent length across multiple devices, increasing the device to device consistency of the manufacturing process. In some instances, the particular lengths of the connecting sleeves are selected to facilitate a desired transition in the stiffness of the distal portion of the intravascular device. In some embodiments, the connecting sleeve 128 is from 1 mm to 20 mm long, and the connecting sleeve 129 is also from 1 mm to 20 mm long. In some embodiments, the connecting sleeve 128 can be larger or smaller than the connecting sleeve 129. In some particular implementations, the connecting sleeve 128 is three times the length of the connecting sleeve 129. However, any combination of lengths for the connecting sleeves 128, 129 can be used in accordance with the present disclosure. As a result of the use of the connecting sleeves 128, 129 and the adhesive 131, there is much greater consistency regarding the length of connection between the core member 126 and the shaping ribbon 127 than there is when coupling the core member 126 and the shaping ribbon 127 with tack soldering. It is understood that in some implementations, the adhesive 131 includes two or more types of adhesive. For example, in some instances the distal connecting sleeve 129 can be filled with a harder durometer adhesive that provides better tensile and shear strength than the a flexible adhesive that is used within the proximal connecting sleeve 128. In this regard, in some instances the proximal connecting sleeve 128 is longer than the distal sleeve 129 and the length of the proximal connecting sleeve 128 can be selected/adjusted to achieve a desired robustness and/or bending transition.

Also, as shown, the proximal and distal flexible elements 120, 122 can be filled, or partially filled, with one or more flexible materials. In the illustrated embodiment, a flexible adhesive 132 fills substantially all of the open space within the lumen of the proximal flexible element 120. In other instances, the lumen of the proximal flexible element 120 is not filled with a flexible material. In the illustrated embodiment, the flexible adhesive 132 partially fills a proximal section of the lumen of the distal flexible element 122. In other instances, the lumen of the distal flexible element 122 is not filled with a flexible material.

The flexible adhesive 132 that partially fills a central lumen of the distal flexible element 122 can be introduced into the lumen of the distal flexible element 122 through the spaces 134 (e.g., by wicking, injecting, flowing, and/or combinations thereof). The adhesive 131 used to fixedly secure the core member 126 and the shaping ribbon 127 together is not introduced into the lumen of the distal flexible element 122 through the spaces 134. In some implementations, the adhesive 131 is introduced and cured to the core member 126 and shaping ribbon 127 as part of a sub-assembly step prior to coupling the distal flexible element 122 and/or the housing 124 to the core member 126 and/or shaping ribbon 127. In other instances, the adhesive 131 can be introduced into the lumen of the distal flexible element 122 through an opening in one of the ends of the distal flexible element 122. For example, in some instances, the adhesive 131 and the flexible adhesive 132 can be introduced into the central lumen of the distal flexible element 122 through an opening in one of the ends of the distal flexible element 122. In some instances, the adhesive 131 and the flexible adhesive 132 are introduced into the central lumen of the distal flexible element 122 after the housing 124 is coupled to the distal flexible element 122 but before the solder ball 130 is coupled to the distal flexible element 122. In some instances, the adhesive 131 and the flexible adhesive 132 are introduced into the central lumen of the distal flexible element 122 after the solder ball 130 is coupled to the distal flexible element 122 but before the housing 124 is coupled to the distal flexible element 122. In other instances, the adhesive 131 and the flexible adhesive 132 are introduced into the central lumen of the distal flexible element 122 before both the solder ball 130 and the housing 124 are coupled to the distal flexible element 122.

In some instances, the adhesive 131 and the flexible adhesive 132 are the same adhesive. In other instances, the adhesive 131 is different than the flexible adhesive 132. In this regard, the flexible adhesive 132 may be chosen to be different than the adhesive 131 in an effort to facilitate a smooth transition in the stiffness of the distal portion of the intravascular device from the housing 124 to the distal flexible element 122. Generally, the adhesives 131 and 132 can be any suitable adhesive, including without limitation, silicone adhesives and urethane adhesives, such as Dymax 1901-M, Dymax 9001, etc., as well as epoxies and acrylates. In some instances, harder durometer adhesives, such as Dymax 1128 or 1184, can be used within the distal connecting sleeve 129.

Figure 5:
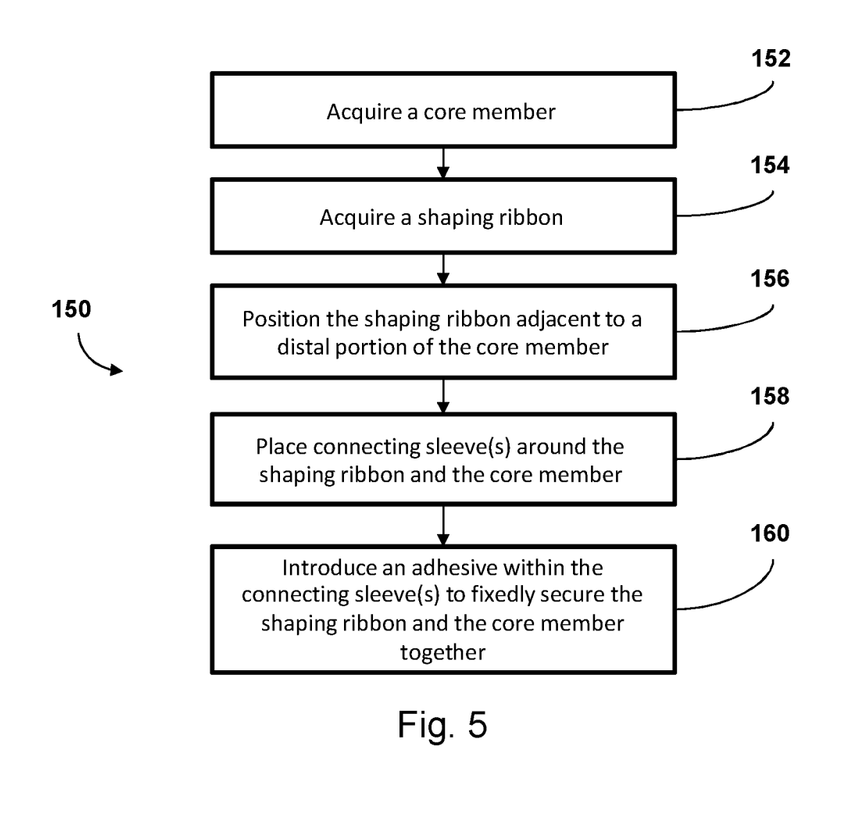
FIG. 5 is a flow diagram of a method of forming an intravascular device according to aspects of the present disclosure.
Figure 6:
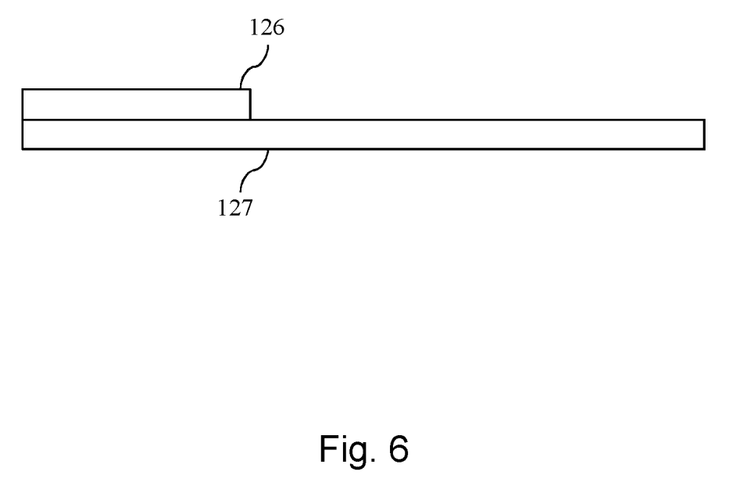
FIG. 6 is a cross-sectional side view of a core member and a shaping ribbon of an intravascular device during a portion of the method of FIG. 5 according to an embodiment of the present disclosure.
Figure 7:
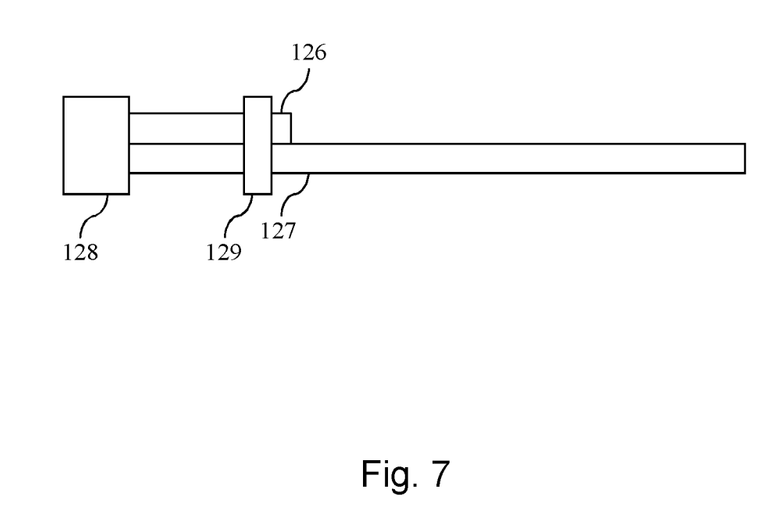
FIG. 7 is a cross-sectional side view of the core member and the shaping ribbon of the intravascular device of FIG. 6 during a subsequent portion of the method of FIG. 5 according to an embodiment of the present disclosure.
Figure 8:
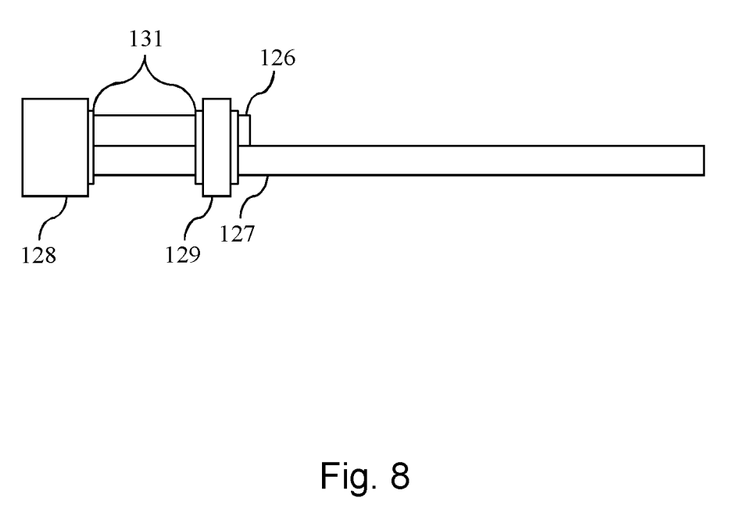
FIG. 8 is a cross-sectional side view of the core member and the shaping ribbon of the intravascular device of FIGS. 6 and 7 during a subsequent portion of the method of FIG. 5 according to an embodiment of the present disclosure.

Referring now to FIGS. 5-8, shown therein are aspects of assembling a section of the distal portion 104 of the intravascular device 100 according to embodiments of the present disclosure. In particular, FIG. 5 is a flow diagram of a method 150 of forming a section of a distal portion of an intravascular device, such as a sensing guide wire, in accordance with the present disclosure, while FIGS. 6-8 illustrate the distal portion 104 at various stages of the method 150.

In this regard, the method 150 can be better understood with reference to FIGS. 6-8. It is understood that the core member 126 and the shaping ribbon 127 can be solid components. Referring again to FIG. 5, the method 150 can include, at step 152, acquiring a core member. With reference now to FIG. 6, the core member 126 can be described herein as a first flexible elongate member. The core member 126 can have a generally constant diameter or a variable diameter/shape. The core member 126 can be formed of a flexible and/or elastic material, including metals or metal alloys such as nickel titanium or nitinol, nickel titanium cobalt, stainless steel, and/or various stainless steel alloys.

Referring again to FIG. 5, the method 150 can include, at step 154, acquiring a shaping ribbon. Referring again to FIG. 6, the shaping ribbon 127 can be described herein as a second flexible elongate member. The shaping ribbon 127 can have a generally constant diameter or a variable diameter/shape. In some implementations, for example, the shaping ribbon 127 and/or the core member 126 can be shaped as described in U.S. Provisional Patent Application No. 62/027,556, filed Jul. 22, 2014, which is hereby incorporated by reference in its entirety. The shaping ribbon 127 can be formed from any suitable material including, for example, a metal or metal alloy such as stainless steel and/or other suitable materials. In some instances, a roller flattened wire is utilized for the shaping ribbon such that the shaping ribbon geometry is wider than it is thick. In this regard, a generally rectangular cross-sectional shape can be preferred to a round or circular cross-sectional shape in some instances.

Referring again to FIG. 5, the method 150 can include, at step 156, positioning the shaping ribbon adjacent to a distal portion of the core member. Referring again to FIG. 6, the shaping ribbon 127 is positioned adjacent to and overlaps the core member 126 such that the shaping ribbon 127 extends beyond the distal end of the core member 126. In some implementations, the shaping ribbon 127 is positioned such that it extends between 0.1 cm and 3.0 cm from the distal end of the core member 126, including 1.0 cm, 1.5 cm, and 2.0 cm in some particular instances. As shown in FIG. 3, a length 146 of the shaping ribbon 127 extends distally from the housing 124. In some instances, the length 146 extends to the distal tip 105 of the distal flexible element 122. In some instances, the length 146 terminates between 0.1 cm and 3.0 cm from the distal end of the core member 126. In some particular implementations, the length 146 is 3 cm. However, any length can be used in accordance with the present disclosure. Also shown in FIG. 3, a length 148 of the core member 126 extends distally from the housing 124. In some instances, the core member 126 extends through the housing 124 and along the entire length of the proximal flexible element 120 such that the core member 126 has a length of about 34 cm. In some instances, the length 148 terminates between 0.1 cm and 3.0 cm proximally before the distal end of the shaping ribbon 127. In some particular implementations, the length 148 is 1 cm. However, any length can be used in accordance with the present disclosure.

Referring again to FIG. 5, the method 150 can include, at step 158, placing connecting sleeve(s) around the shaping ribbon and the core member. Referring now to FIG. 7, in the illustrated embodiment two connecting sleeves 128, 129 are placed around the shaping ribbon 127 and the core member 126. The connecting sleeve 128 can be positioned around the core member 126 and the shaping ribbon 127 at a proximal portion of the shaping ribbon 127. The connecting sleeve 129 can be positioned around the core member 126 and the shaping ribbon 127 at a distal portion of the core member 126. The connecting sleeve 128 can be positioned around the core member 126 and the shaping ribbon 127 before the connecting sleeve 129, vice versa, or simultaneously. In some embodiments, there can be more than two connecting sleeves. The lengths and positioning of the connecting sleeves 128, 129 along the core member 126 and the shaping ribbon 127 can be controlled in a more consistent manner than trying to control the length of a solder joint. This allows for the connection points between the core member 126 and the shaping ribbon 127 to be replicated with better accuracy than if the core member 126 and shaping ribbon 127 were coupled with a solder joint.

Referring again to FIG. 5, the method 150 can include, at step 160, introducing an adhesive within the connecting sleeve(s) to fixedly secure the shaping ribbon and the core member together. Referring now to FIG. 8, in the illustrated embodiment an adhesive 131 can be introduced in the space between the connecting sleeves 128, 129 and the core member 126 and the shaping ribbon 127. When cured, the adhesive 131 fixedly secures the core member 126 and the shaping ribbon 127 together. The adhesive 131 can be introduced within the connecting sleeves 128, 129 by wicking, injecting, flowing, and/or combinations thereof. In some implementations, the connecting sleeves 128, 129 can be removed after the adhesive 131 has been cured. In this regard, the adhesive 131 may be cured by heat, light, UV, and/or combinations thereof. Further, in some implementations, different adhesives may be used within different connecting sleeves. In other implementations, the same adhesive is utilized in all of the connecting sleeves.

In some embodiments, the method 150 and associated steps of coupling the shaping ribbon 127 to the core member 126 can be performed before, after, or concurrently with coupling the core member 126 and/or the shaping ribbon 127 to other components of the intravascular device 100. In some instances, the method 150 and associated steps of coupling the shaping ribbon 127 to the core member 126 can be performed before, after, or concurrently with coupling/soldering the shaping ribbon 127 to the distal tip 105, coupling/soldering the distal flexible element 122 to the housing 124, coupling/soldering the distal flexible element 122 to the distal tip 105, coupling the core member 126 to the housing 124, coupling the core member 126 to the proximal flexible element 120, coupling/soldering the flexible elongate member 102 to the connector 110, and coupling/soldering any other components of the intravascular device 100 in accordance with the present disclosure.

In some embodiments, the method 150 can include additional steps to incorporate the component 108 within the intravascular device 100. For example, the method 150 can include coupling the housing 124 to the core member 126, when the housing 124 is a separate component. The method 150 can include forming a recess within the core member 126. The recess can be sized and shaped to accommodate the component 108. The method 150 can also include coupling the component 108 to the core member 126 (e.g., within the housing 124 or within the recess formed within the core member 126). The component 108 can be positioned at a distal portion of the core member 126. The method 150 can include various other steps to complete assembly of the intravascular device 100, including electrically coupling the component 108 to other component(s) of the intravascular device 100, introducing adhesive(s) into a lumen of the flexible elongate member 102, coupling the proximal and distal flexible elements 120, 122, introducing a sleeve (e.g., with an integrated coil) around the flexible elongate member 102, introducing a tip coil around the distal portion 104, among others.

Guide wires of the present disclosure can be connected to an instrument, such as a computing device (e.g., a laptop, desktop, or tablet computer) or a physiology monitor, that converts the signals received by the sensors into pressure and velocity readings. The instrument can further calculate Coronary Flow Reserve (CFR) and Fractional Flow Reserve (FFR) and provide the readings and calculations to a user via a user interface. In some embodiments, a user interacts with a visual interface to view images associated with the data obtained by the intravascular devices of the present disclosure. Input from a user (e.g., parameters or a selection) are received by a processor in an electronic device. The selection can be rendered into a visible display.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. For example, the features of various embodiments can be combined with features of different embodiments. One or more steps can be added to or removed from the methods described herein. A person of ordinary skill in the art will understand that the steps of the method can be performed in an order different than the order described herein. It is understood that such variations may be made to the foregoing without departing from the scope of the present disclosure. Accordingly, it is appropriate that the appended claims be construed broadly and in a manner consistent with the present disclosure.

What is claimed is:

1. A sensing guide wire, comprising:
    a flexible elongate member comprising a proximal portion and a distal portion;
    a housing structure coupled to the distal portion of the flexible elongate member; and
    a sensing element disposed within the housing structure,
    wherein the distal portion of the flexible elongate member includes:
        a core member; and
        a shaping ribbon comprising:
            a proximal end at a proximal-most point of the shaping ribbon;
            a distal end at a distal-most point of the shaping ribbon;
            a length that extends from the proximal-most point to the distal-most point of the shaping ribbon; and
            a flattened shape comprising a thickness and a width larger than the thickness, wherein a size of the flattened shape is the same at every point along the length of the shaping ribbon from the proximal-most point to the distal-most point,
    wherein the shaping ribbon is fixedly secured to the core member by an adhesive and a connecting sleeve such that the connecting sleeve is disposed distal to and spaced from the sensing element.

2. The guide wire of claim 1, wherein the core member is formed of nitinol.

3. The guide wire of claim 1, further comprising a rounded tip coupled to the distal portion of the flexible elongate member, wherein the rounded tip is soldered to the distal portion of the flexible elongate member.

4. The guide wire of claim 1, wherein the shaping ribbon extends distally from the core member.

5. The guide wire of claim 1, wherein the adhesive includes an adhesive selected from a group of adhesives consisting of urethane adhesives, silicon adhesives, epoxies, and acrylates.

6. The guide wire of claim 1, wherein the connecting sleeve comprises a polymer connecting sleeve.

7. The guide wire of claim 1, wherein the sensing element includes a pressure sensor or a flow sensor.

8. The guide wire of claim 1, wherein the shaping ribbon is coupled to the housing structure.

9. The guide wire of claim 8, wherein the connecting sleeve is positioned around the core member and a first segment of the length of the shaping ribbon.

10. The guide wire of claim 9, wherein the connecting sleeve is secured around an outer surface of the first segment of the length of the shaping ribbon and an outer surface of the core member.

11. The guide wire of claim 9, wherein a second segment of the length of the shaping ribbon extends:
    proximally from the connecting sleeve;
    proximate to the core member; and
    between the housing structure and the connecting sleeve.

12. The guide wire of claim 11,
    wherein the shaping ribbon is fixedly secured to the core member by the adhesive and a plurality of connecting sleeves,
    wherein the plurality of connecting sleeves comprises the connecting sleeve and an additional connecting sleeve spaced from the connecting sleeve.

13. The guide wire of claim 12, wherein a first length of the connecting sleeve is configured to provide a first stiffness at a first location of the distal portion of the flexible elongate member and a second length of the additional connecting sleeve is configured to provide a second stiffness at a second location of the distal portion of the flexible elongate member.

14. The guide wire of claim 13, wherein the first length is different from the second length.

15. The guide wire of claim 12,
wherein the shaping ribbon is fixedly secured to the core member by the adhesive and an additional adhesive different from the adhesive,
wherein the adhesive is disposed within the connecting sleeve and the additional adhesive is disposed within the additional connecting sleeve.

16. The guide wire of claim 12, wherein the additional connecting sleeve is disposed distal to the sensing element.

17. The guide wire of claim 12, wherein a second segment of the shaping ribbon extends between the connecting sleeve and the additional connecting sleeve.

18. The guide wire of claim 1,
wherein the proximal end of the shaping ribbon is proximal of and spaced from a portion of the core member around which the connecting sleeve is positioned, and
wherein a proximal portion of the connecting sleeve is proximal of a distal end of the core member.

19. The guide wire of claim 1, wherein the connecting sleeve is positioned around a distal end of the core member.

20. The guide wire of claim 1, wherein the shaping ribbon is formed of stainless steel.

* * * * *